(12) United States Patent
Zhu (10) Patent No.: US 12,115,099 B2
(45) Date of Patent: *Oct. 15, 2024

(54) COMBINED TYPE HAND WARMER (71) Applicant: Guangdong Aoyun Technology Co., Ltd., Guangdong (CN)

(72) Inventor: Xueping Zhu, Guangdong (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/514,327

(22) Filed: Nov. 20, 2023

(65) Prior Publication Data

US 2024/0122747 A1    Apr. 18, 2024

Related U.S. Application Data

(63) Continuation-in-part of application No. 17/967,744, filed on Oct. 17, 2022, now Pat. No. 11,916,334.

(51) Int. Cl.
| H05B 3/06 | (2006.01) |
| A44B 11/00 | (2006.01) |
| A61F 7/08 | (2006.01) |
| A61F 7/00 | (2006.01) |

(52) U.S. Cl.
CPC .............. *A61F 7/08* (2013.01); *A44B 11/005* (2013.01); *A61F 2007/0036* (2013.01); *A61F 2007/0078* (2013.01); *A61F 2007/0087* (2013.01)

(58) Field of Classification Search
None
See application file for complete search history.

(56) References Cited

FOREIGN PATENT DOCUMENTS

| CN | 103411260 A | † 11/2013 |
| CN | 204951305 U | † 1/2016 |
| CN | 207949984 U | † 10/2018 |
| CN | 210320254 U | † 4/2020 |
| CN | 210784976 U | † 6/2020 |
| CN | 211244016 U | † 8/2020 |
| CN | 213285543 U | * 5/2021 |
| CN | 219847034 U | † 10/2023 |
| CN | 219940987 U | † 11/2023 |
| CN | 220695427 U | † 4/2024 |
| KR | 20160001001 U | * 3/2016 |
| KR | 101989309 B1 | * 6/2019 |

OTHER PUBLICATIONS

KR101989309, Jun. 4, 2019, partial translation (Year: 2019).*
KR20160001001, Mar. 29, 2016, partial translation (Year: 2016).*

* cited by examiner
† cited by third party

*Primary Examiner* — Dana Ross
*Assistant Examiner* — Lawrence H Samuels (57) ABSTRACT

The present disclosure provides a combined type hand warmer, including a first hand warmer unit and a second hand warmer unit; a first connection part is arranged on the first hand warmer unit, and a second connection part is arranged on the second hand warmer unit; the first connection part is detachably connected to the second connection part such that the first hand warmer unit and the second hand warmer unit are combined into a whole; and when a user needs to warm two hands/multiple body parts, the first hand warmer unit can be separated from the second hand warmer unit, and the first hand warmer unit and the second hand warmer unit can be respectively used for warming the two hands/multiple body parts.

12 Claims, 7 Drawing Sheets

COMBINED TYPE HAND WARMER

CROSS-REFERENCE TO RELATED APPLICATIONS

This application is a Continuation-in-Part of the U.S. application Ser. No. 17/967,744 filed on Oct. 17, 2022, and entitled "COMBINED TYPE HAND WARMER," now pending, the entire disclosures of which are incorporated herein by reference.

TECHNICAL FIELD

The present disclosure relates to the field of hand warmers, in particular, to a combined type hand warmer.

BACKGROUND

Existing hand warmers on the market, whether they are double-sided or single-sided, can usually only be used for warming one hand/one body part, and it is difficult to warm both hands/multiple body parts at the same time. Particularly, when a user has to do different actions with two hands or when a plurality of parts of the user need to be warmed, the current hand warmer can hardly meet the need of the user. Therefore, there is an urgent need to provide a hand warmer that can be used for warming two hands/multiple body parts at the same time and is easy for users to carry.

SUMMARY

In order to overcome the defects of the prior art, the present disclosure provides a combined type hand warmer, which can be used for warming two hands/multiple body parts and is convenient for a user to carry.

The present disclosure adopts the following technical solution:

The present disclosure provides a combined type hand warmer, including a first hand warmer unit and a second hand warmer unit, wherein the first hand warmer unit includes a first outer surface and a first connection inner surface opposite to the first outer surface, the second hand warmer unit includes a second outer surface and a second connection inner surface opposite to the second outer surface; the first connection inner surface includes a first connection part, the second connection inner surface includes a second connection part, and the first connection part is connected to the second connection part by buckling or magnetic attraction, so that the first connection inner surface is connected to the second connection inner surface, and the first hand warmer unit and the second hand warmer unit are combined into a whole.

As the improvement of the present disclosure, the first connection part is connected to the second connection part by buckling, the first connection part includes a first buckling part, the second connection part includes a first buckle matching part, the first buckling part is detachably connected to the first buckle matching part, so that the first connection inner surface is buckled with the second connection inner surface, and the first hand warmer unit and the second hand warmer unit are combined into a whole.

As the improvement of the present disclosure, the first connection part further includes a second buckling part, the second connection part further includes a second buckle matching part, and when the first buckling part is detachably plugged into the first buckle matching part, the second buckling part is detachably plugged into the second buckle matching part.

As the improvement of the present disclosure, the first buckling part is a buckle or a buckle slot, the first buckle matching part is a buckle and a buckle slot, and when the first buckling part is a buckle, the first buckle matching part is a buckle slot; when the first buckling part is a buckle slot, the first buckle matching part is a buckle; the second buckling part is a buckle or a buckle slot, the second buckle matching part is a buckle and a buckle slot, and when the second buckling part is a buckle, the second buckle matching part is a buckle slot; and when the second buckling part is a buckle slot, the second buckle matching part is a buckle.

As the improvement of the present disclosure, the first buckling part is a first buckle, the first buckle matching part is a first buckle slot, and the first buckle is detachably plugged into the first buckle slot.

As the improvement of the present disclosure, the second buckling part is a second buckle slot, the second buckle matching part is a first buckle, and when the first buckle is detachably plugged into the first buckle slot, the second buckle is detachably plugged into the second buckle slot.

As the improvement of the present disclosure, the first connection part further includes a first positioning pillar, the second connection part further includes a first positioning hole, when the first positioning pillar is located in the first positioning hole, the first buckle is detachably plugged into the first buckle slot, and the second buckle is detachably plugged into the second buckle slot. The first connection part further includes a second positioning hole, the second connection part further includes a second positioning pillar, and when the first positioning pillar is located in the first positioning hole and the second positioning pillar is located in the second positioning hole, the first buckle is detachably plugged into the first buckle slot, and the second buckle is detachably plugged into the second buckle slot. The first connection part further includes a first guide slot, the first positioning pillar is located on an upper side of the first guide slot, the second positioning hole is located on a lower side of the first guide slot, the second connection part further includes a second guide slot, the first positioning hole is located on an upper side of the second guide slot, the second positioning pillar is located on a lower side of the first guide slot, when the first positioning pillar slides into the first positioning hole along the second guide slot and the second positioning pillar slides into the second positioning hole along the first guide slot, the first buckle is detachably plugged into the first buckle slot, and the second buckle is detachably plugged into the second buckle slot.

As the improvement of the present disclosure, the first buckle is arranged on one side of the first hand warmer unit, the second buckle slot is symmetrically arranged on the other side of the first hand warmer unit; the second buckle is arranged on one side of the second hand warmer unit, and the first buckle slot is symmetrically arranged on the other side of the second hand warmer unit.

As the improvement of the present disclosure, the first outer surface of the first hand warmer unit is further provided with a first charging port, the first charging port is used for charging the first hand warmer unit; the second outer surface of the second hand warmer unit is further provided with a second charging port, and the second charging port is used for charging the second hand warmer unit.

As the improvement of the present disclosure, the first buckling part is a rotatable buckle, the first buckle matching part is a slot, and the rotatable buckle is detachably connected to the slot.

As the improvement of the present disclosure, a stop lug is arranged on the rotatable buckle, a stop edge is arranged on the slot, a notch is arranged on the stop edge, the notch is communicated with the slot, when the stop lug rotates to the notch with the rotatable buckle, the stop lug is placed in the slot along with the rotatable buckle through the notch; when the stop lug is placed in the slot along with the rotatable buckle through the notch, the rotatable buckle is rotated so that the stop lug is rotated to stagger with the notch, the stop edge stops the stop lug of the rotatable buckle in the slot, and the first hand warmer unit and the second hand warmer unit are combined into a whole.

As the improvement of the present disclosure, a first power indicator is further arranged on the first hand warmer unit, the first power indicator is used for displaying the battery power of the first hand warmer unit; a second power indicator is further arranged on the second hand warmer unit, and the second power indicator is used for displaying the battery power of the second hand warmer unit.

As the improvement of the present disclosure, a first on/off button is further arranged on the first hand warmer unit, the first on/off button is used for controlling the first hand warmer unit to be turned on/off; a second on/off button is further arranged on the second hand warmer unit, and the second on/off button is used for controlling the second hand warmer unit to be turned on/off.

As the improvement of the present disclosure, the first connection part is connected to the second connection part by magnetic attraction, the first connection part includes a first magnetic attraction element, the second connection part includes a first magnetic attraction matching element, and the first magnetic attraction element and the first magnetic attraction matching element are mutually attracted, so that the first connection inner surface is attached to the second connection inner surface, and the first hand warmer unit and the second hand warmer unit are combined into a whole.

The present disclosure has the beneficial effects: the combined type hand warmer includes the first hand warmer unit and the second hand warmer unit; the first connection part is arranged on the first hand warmer unit, and the second connection part is arranged on the second hand warmer unit; and the first connection part is detachably connected to the second connection part such that the first hand warmer unit and the second hand warmer unit are combined into a whole. Therefore, when a user needs to warm two hands/multiple body parts, the first hand warmer unit can be separated from the second hand warmer unit, and the first hand warmer unit and the second hand warmer unit can be respectively used for warming the two hands/multiple body parts. When the user only needs to warm one hand/one body part, the first connection part can be connected to the second connection part to combine the first hand warmer unit with the second hand warmer unit into a whole, so as to enlarge a warming area of the hand warmer for one hand/one body part and enhance the warming effect. Furthermore, when the user needs to carry or store the hand warmer, the user selects, according to an actual situation, either to separately carry or store the first hand warmer and the second hand warmer, or to carry or store the first hand warmer and the second hand warmer as a whole, so as to satisfy a plurality of use scenarios of the user and greatly improve the experience of the user.

BRIEF DESCRIPTION OF THE DRAWINGS

Implementations of the present disclosure will now be described, by way of embodiment, with reference to the attached figures. It should be understood, the drawings are shown for illustrative purpose only, for ordinary person skilled in the art, other drawings obtained from these drawings without paying creative labor by an ordinary person skilled in the art should be within scope of the present disclosure.

DETAILED DESCRIPTION OF THE EMBODIMENTS

Referring to FIG. 1 to FIG. 5, a combined type hand warmer includes a first hand warmer unit 1 and a second hand warmer unit 2; a first connection part 3 is arranged on the first hand warmer unit 1, and a second connection part 4 is arranged on the second hand warmer unit 2; and the first connection part 3 is detachably connected to the second connection part 4 such that the first hand warmer unit 1 and the second hand warmer unit 2 are combined into a whole. By the above structure, the combined type hand warmer includes the first hand warmer unit and the second hand warmer unit; the first connection part is arranged on the first hand warmer unit, and the second connection part is arranged on the second hand warmer unit; and the first connection part is detachably connected to the second connection part such that the first hand warmer unit and the second hand warmer unit are combined into a whole. Therefore, when a user needs to warm two hands/multiple body parts, the first hand warmer unit can be separated from the second hand warmer unit, and the first hand warmer unit and the second hand warmer unit can be respectively used for warming the two hands/multiple body parts. When the user only needs to warm one hand/one body part, the first connection part can be connected to the second connection part to combine the first hand warmer unit with the second hand warmer unit into a whole, so as to enlarge a warming area of the hand warmer for one hand/one body part and enhance the warming effect. Furthermore, when the user needs to carry or store the hand warmer, the user selects, according to an actual situation, either to separately carry or store the first hand warmer and the second hand warmer, or to carry or store the first hand warmer and the second hand warmer as a whole, so as to satisfy a plurality of use scenarios of the user and greatly improve the experience of the user.

In this embodiment, the first hand warmer unit 1 comprises a first outer surface 14 and a first connection inner surface 15 opposite to the first outer surface 14. The second hand warmer unit comprises a second outer surface 24 and a second connection inner surface 25 opposite to the second outer surface 24. The first connection inner surface 15 comprises a first connection part 3. The second connection inner surface 25 comprises a second connection part 4. The first connection part 3 comprises a first buckling part. The second connection part 4 comprises a first buckle matching part. The first buckling part is detachably connected to the first buckle matching part, so that the first connection inner surface 15 is buckled with the second connection inner surface 25. The first hand warmer unit 1 and the second hand warmer unit 2 are combined into a whole.

The first connection part 3 is connected to the second connection part 4 by buckling or magnetic attraction, so that the first connection inner surface 15 is connected to the second connection inner surface 25. The first hand warmer unit 1 and the second hand warmer unit 2 are combined into a whole.

Specifically, referring to FIGS. 1 to 5, in some embodiments, the first connection part 3 is connected to the second connection part 4 by buckling. The first connection part 3 further comprises a second buckling part. The second connection part 4 further comprises a second buckle matching part. When the first buckling part is detachably plugged into the first buckle matching part, the second buckling part is detachably plugged into the second buckle matching part.

Specifically, the first buckling part is a buckle or a buckle slot. The first buckle matching part is a buckle and a buckle slot. When the first buckling part is a buckle, the first buckle matching part is a buckle slot. When the first buckling part is a buckle slot, the first buckle matching part is a buckle. The second buckling part is a buckle or a buckle slot. The second buckle matching part is a buckle and a buckle slot. When the second buckling part is a buckle, the second buckle matching part is a buckle slot. When the second buckling part is a buckle slot, the second buckle matching part is a buckle.

In this embodiment, the first buckling part is a first buckle 31. The first buckle matching part is a first buckle slot 41. The first buckle 31 is detachably plugged into the first buckle slot 41. The second buckling part is a second buckle slot 32. The second buckle matching part is a first buckle 42. When the first buckle 31 is detachably plugged into the first buckle slot 41, the second buckle 42 is detachably plugged into the second buckle slot 32. By the above structure, the structure is simple, and the connection is stable, so that the detachable connection between the first connection part and the second connection part is effectively achieved. Furthermore, in this embodiment, the first connection part and the second connection part can also be detachably connected using a detachable manner such as male and female fasteners, hook and loop fasteners and the like.

In this embodiment, the first connection part 3 further comprises a first positioning pillar 33. The second connection part 4 further comprises a first positioning hole 43. When the first positioning pillar 33 is located in the first positioning hole 43, the first buckle 31 is detachably plugged into the first buckle slot 41, and the second buckle 42 is detachably plugged into the second buckle slot 32. The first connection part 3 further comprises a second positioning hole 34. The second connection part 4 further comprises a second positioning pillar 44. When the first positioning pillar 33 is located in the first positioning hole 43 and the second positioning pillar 44 is located in the second positioning hole 34, the first buckle 31 is detachably plugged into the first buckle slot 41, and the second buckle 42 is detachably plugged into the second buckle slot 32. Specifically, the first connection part 3 further comprises a first guide slot 35. The first positioning pillar 33 is located on an upper side of the first guide slot 35. The second positioning hole 34 is located on a lower side of the first guide slot 35. The second connection part 4 further comprises a second guide slot 45. The first positioning hole 43 is located on an upper side of the second guide slot 45. The second positioning pillar 44 is located on a lower side of the first guide slot 45. When the first positioning pillar 33 slides into the first positioning hole 43 along the second guide slot 45 and the second positioning pillar 44 slides into the second positioning hole 34 along the first guide slot 35, the first buckle 31 is detachably plugged into the first buckle slot 41, and the second buckle 42 is detachably plugged into the second buckle slot 32. Further, the first buckle 31 is arranged on one side of the first hand warmer unit 1. The second buckle slot 32 is symmetrically arranged on the other side of the first hand warmer unit 1. The second buckle 42 is arranged on one side of the second hand warmer unit 2, and the first buckle slot 41 is symmetrically arranged on the other side of the second hand warmer unit 2. By the above structure, it can ensure, by means of the connection between the first positioning pillar and the first positioning hole, and the connection between the second positioning pillar and the second positioning hole, that the first buckle is fully plugged into the first buckle slot, and the second buckle is fully plugged into the second buckle slot, so as to improve the stability of the connection between the first hand warmer unit and the second hand warmer unit. Furthermore, the first guide slot can ensure that the second positioning pillar quickly and accurately slides into the second positioning hole, and the second guide slot can ensure that the first positioning pillar quickly and accurately slides into the first positioning hole, so as to quickly and accurately plug the first buckle into the first buckle slot and plug the second buckle into the second buckle slot to complete connection between the first hand warmer unit and the second hand warmer unit and combine the first hand warmer unit with the second hand warmer unit into a whole. Further, the first positioning pillar is located in the first positioning hole, and the second positioning pillar is located in the second positioning hole, which can effectively prevent the first positioning pillar from sliding out of the first positioning hole and prevent the second positioning pillar from sliding out of the second positioning hole, thus preventing relative sliding between the first hand warmer unit and the second hand warmer unit and preventing the first hand warmer unit from being loosened from the second hand warmer unit. Much further, when the user needs to separate the first hand warmer unit from the second hand warmer unit, the user only needs to slide the first positioning pillar out of the first positioning hole and slide the second positioning pillar out of the second positioning hole, so as to slide the first buckle out of the first buckle slot and slide the second buckle out of the second buckle slot, thus completing the separation of the first hand warmer unit from the second hand warmer unit. It is convenient for the user to use the first hand warmer unit and the second hand warmer unit to warm multiple body parts, and the first hand warmer unit and the second hand warmer unit can even be provided for different people for use; meanwhile, it is also convenient for the user to separately carry and store the first hand warmer unit and the second hand warmer unit, and the user can even carry the first hand warmer unit and the second hand warmer unit separately after putting them in pockets.

Figure 1:
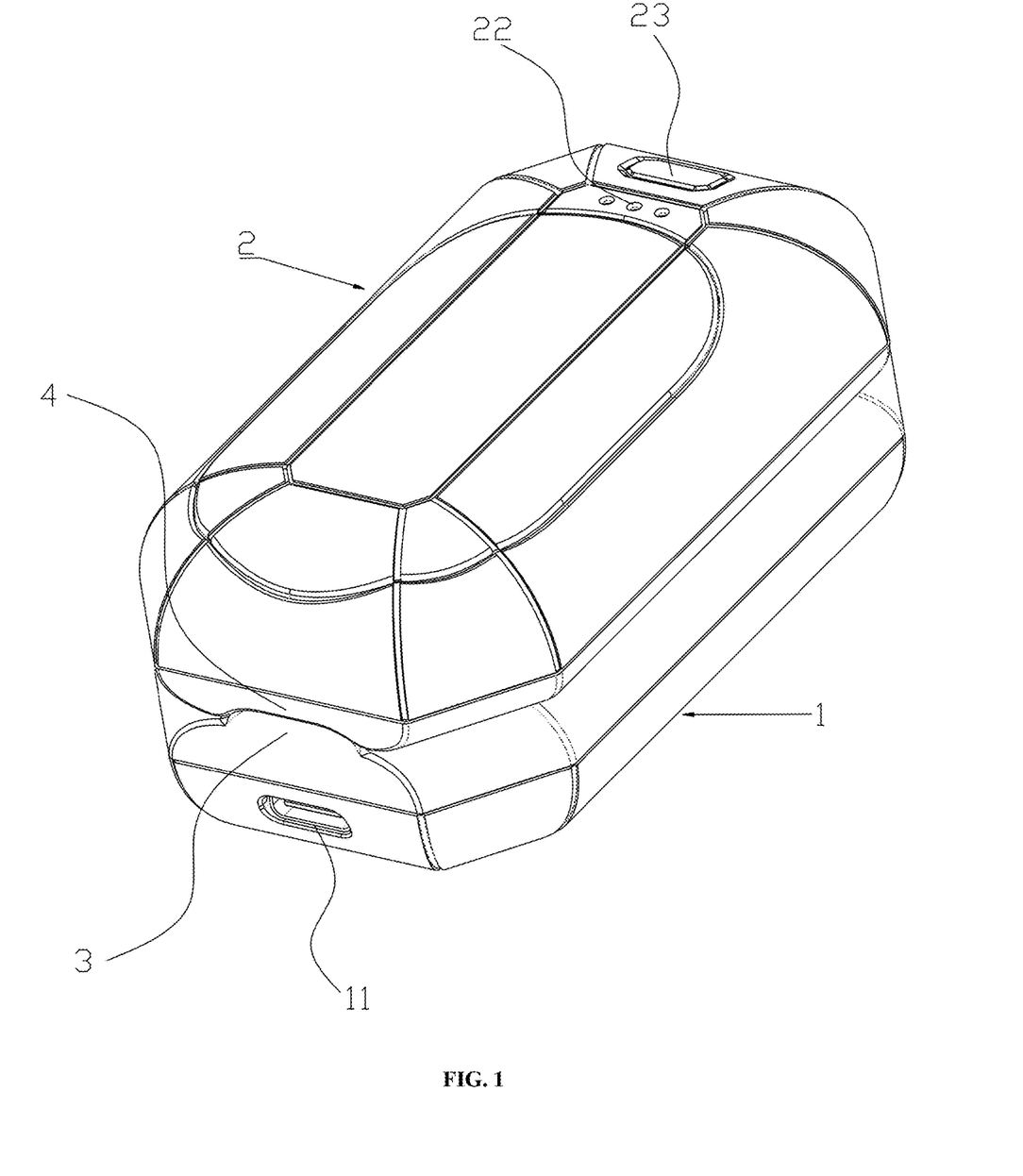
FIG. 1 is a schematic diagram of an overall structure of the present utility model.
Figure 2:
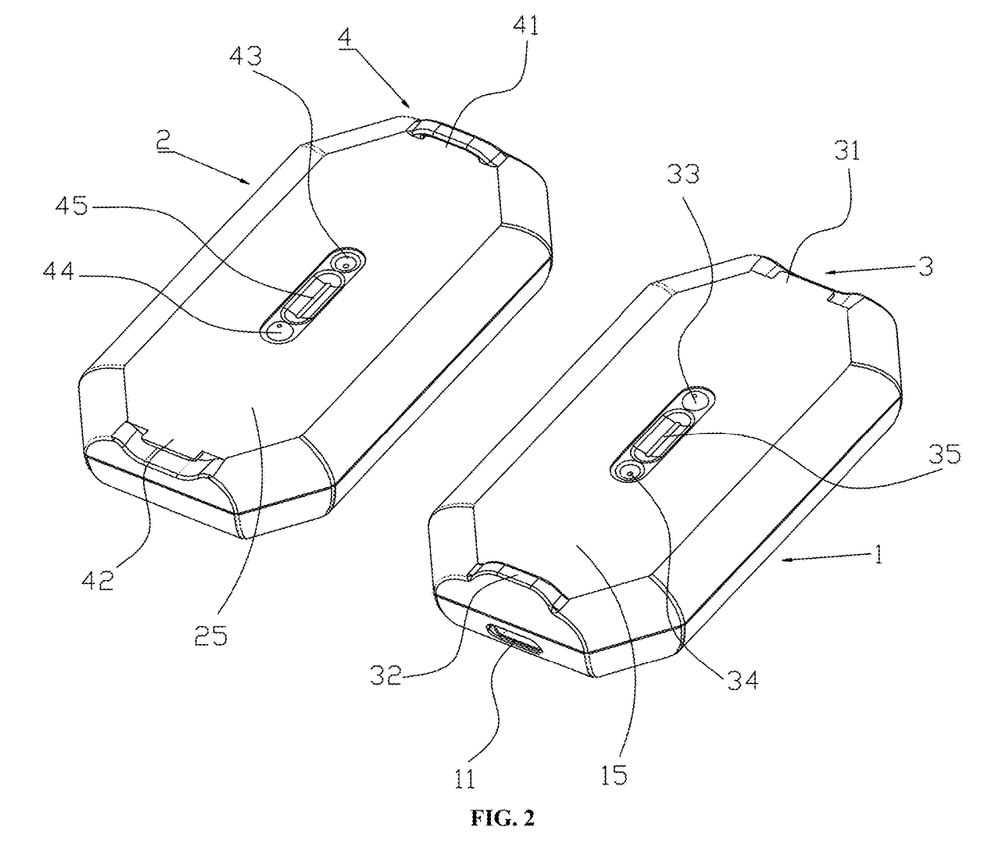
FIG. 2 is an exploded diagram of the present utility model.
Figure 3:
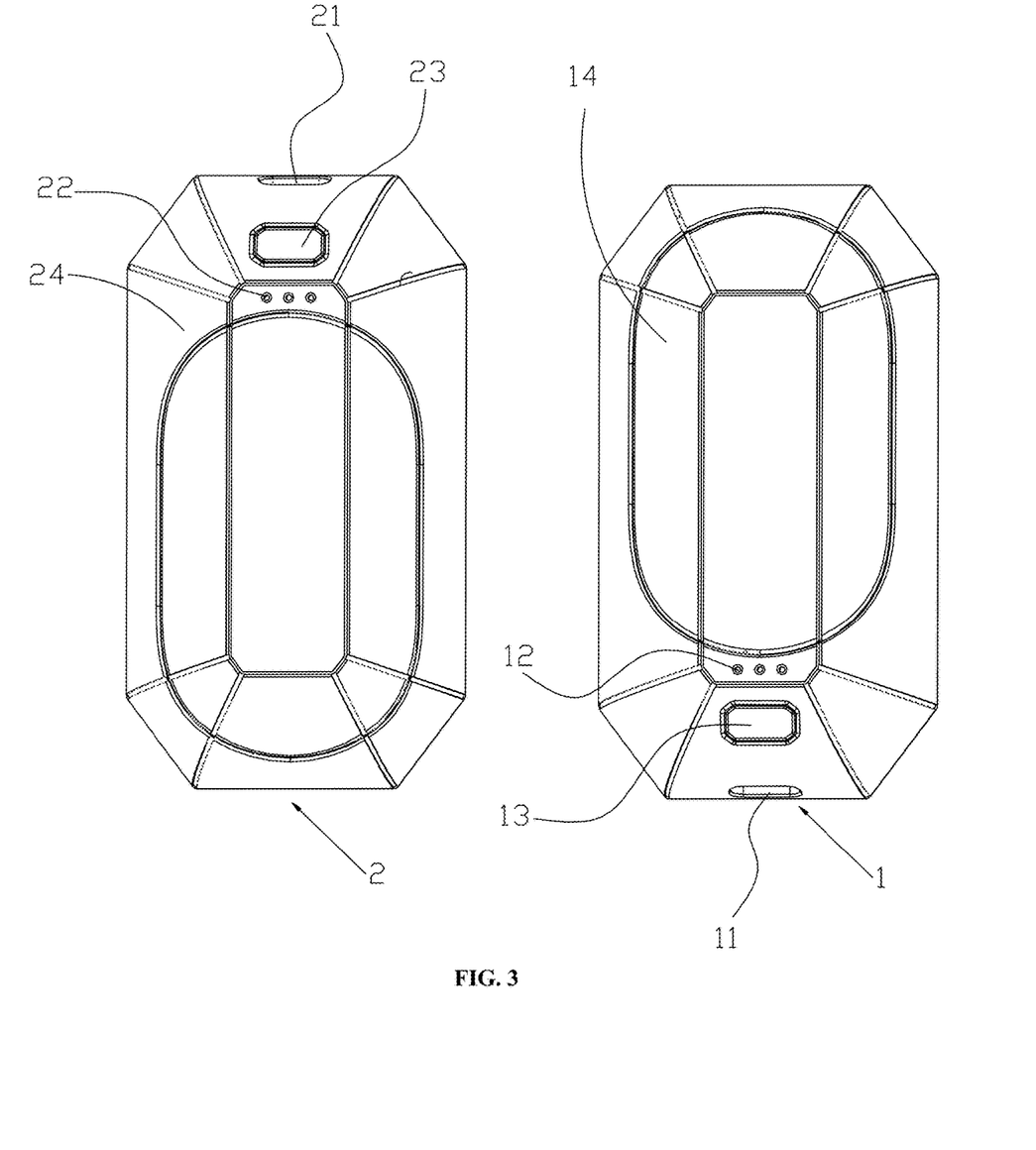
FIG. 3 is another exploded diagram of the present utility model.
Figure 4:
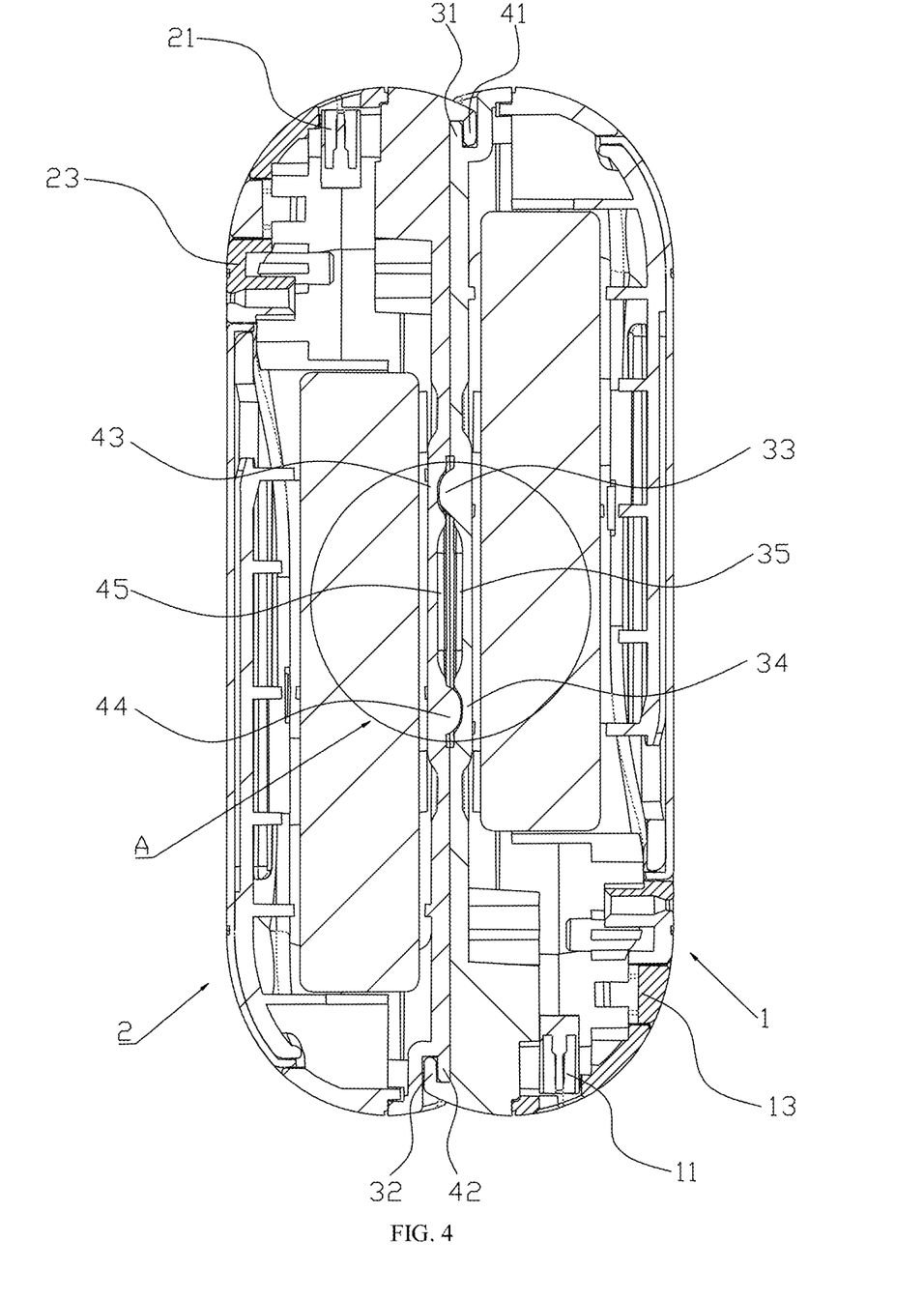
FIG. 4 is a sectional view sectioning along a first connection part and a second connection part.
Figure 5:
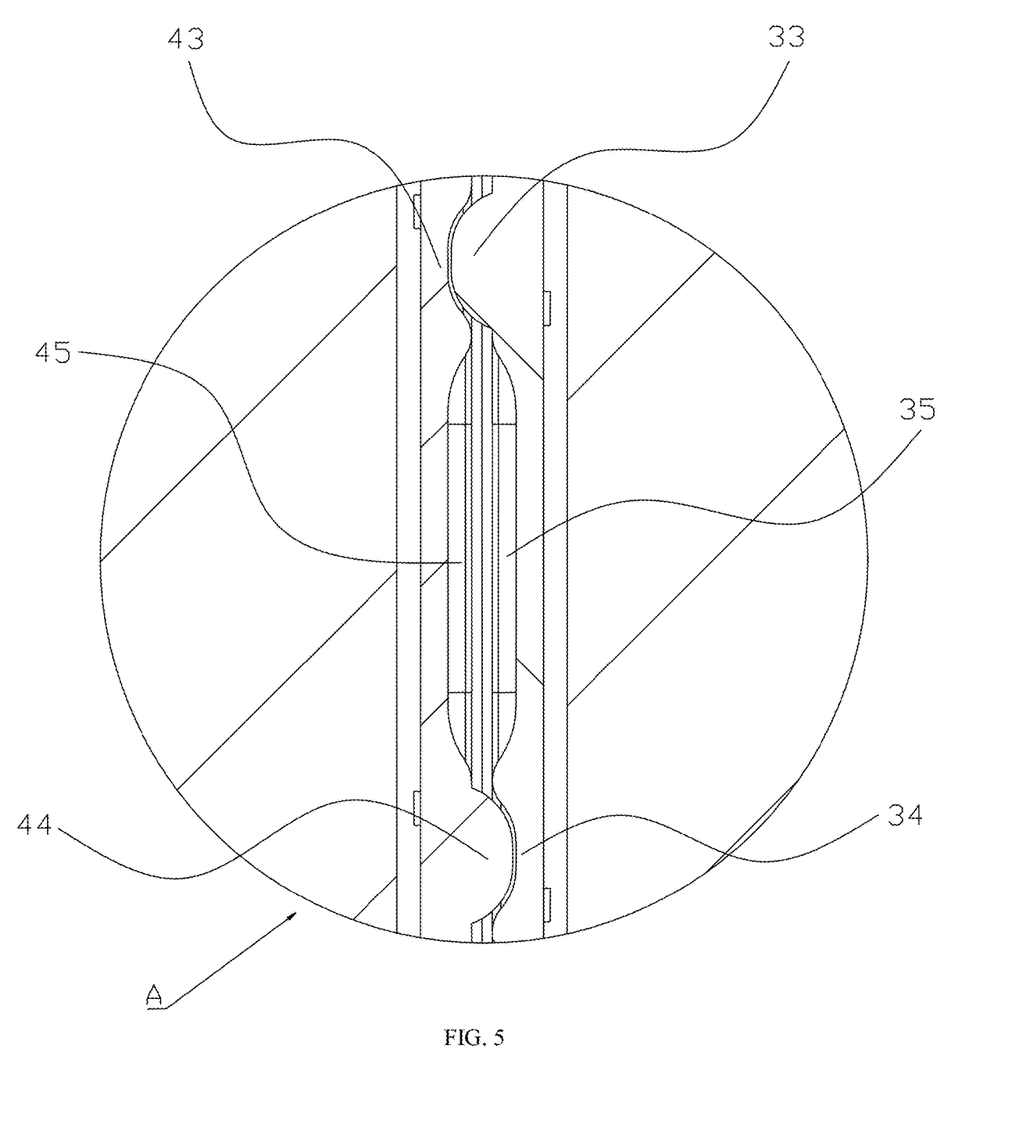
FIG. 5 is an enlarged diagram of the part A of FIG. 4.

In this embodiment, the first outer surface 14 of the first hand warmer unit 1 is further provided with a first charging port 11. The first charging port 11 is used for charging the first hand warmer unit 1. The second outer surface 24 of the second hand warmer unit 2 is further provided with a second charging port 21, and the second charging port 21 is used for charging the second hand warmer unit 2. A first power indicator 12 is further arranged on the first hand warmer unit 1. The first power indicator 12 is used for displaying the battery power of the first hand warmer unit 1. A second power indicator 22 is further arranged on the second hand warmer unit 2, and the second power indicator 22 is used for displaying the battery power of the second hand warmer unit 2. Specifically, a first on/off button 13 is further arranged on the first hand warmer unit 1. The first on/off button 13 is used for controlling the first hand warmer unit 1 to be turned on/off. A second on/off button 23 is further arranged on the second hand warmer unit 2, and the second on/off button 23 is used for controlling the second hand warmer unit 2 to be turned on/off. By the above structure, the user can charge the first hand warmer unit through the first charging port and charge the second hand warmer unit through the second charging port, and can observe the residual battery power of the first hand warmer unit through the first power indicator and observe the residual battery power of the second hand warmer unit through the second power indicator. Further, the user can further select to power on or off the first hand warmer unit through the first on/off button and select to power on or off the second hand warmer unit through the second on/off button.

Figure 6:
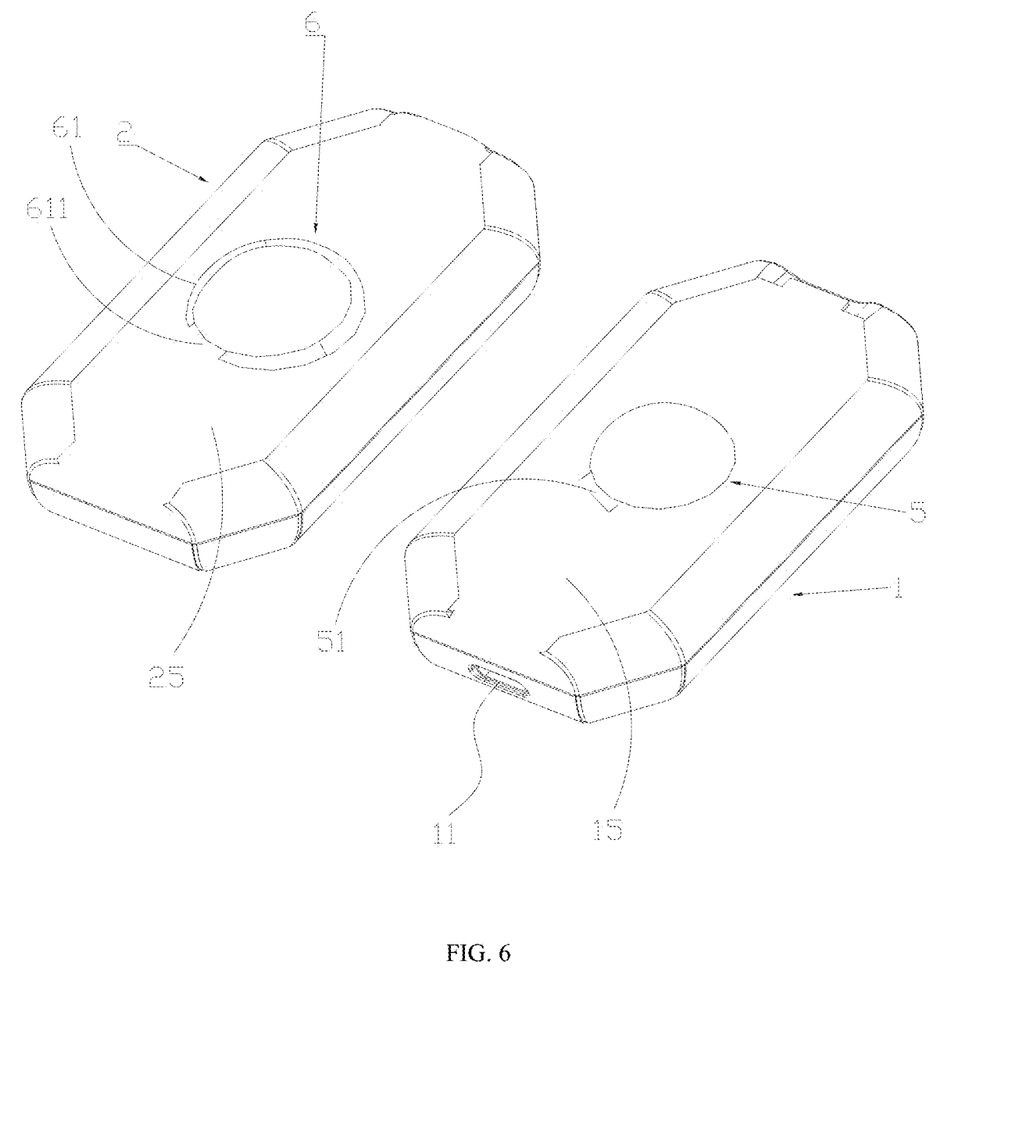
FIG. 6 is a schematic structural diagram of a slot and a rotatable buckle.

Referring to FIG. 6, in some embodiments, the first buckling part is a rotatable buckle 5. The first buckle matching part is a slot 6. The rotatable buckle 5 is detachably connected to the slot 6. A stop lug 51 is arranged on the rotatable rotatable buckle 5. A stop edge 61 is arranged on the slot 6. A notch 611 is arranged on the stop edge 61. The notch 611 is communicated with the slot 6. When the stop lug 51 rotates to the notch 611 with the rotatable buckle 5, the stop lug 51 is placed in the slot 6 along with the rotatable buckle 5 through the notch 611. When the stop lug 51 is placed in the slot 6 along with the rotatable buckle 5 through the notch 611, the rotatable buckle 5 is rotated so that the stop lug 51 is rotated to stagger with the notch 611, the stop edge 61 stops the stop lug 51 of the rotatable buckle 5 in the slot 6, and the first hand warmer unit 1 and the second hand warmer unit 2 are combined into a whole.

Figure 7:
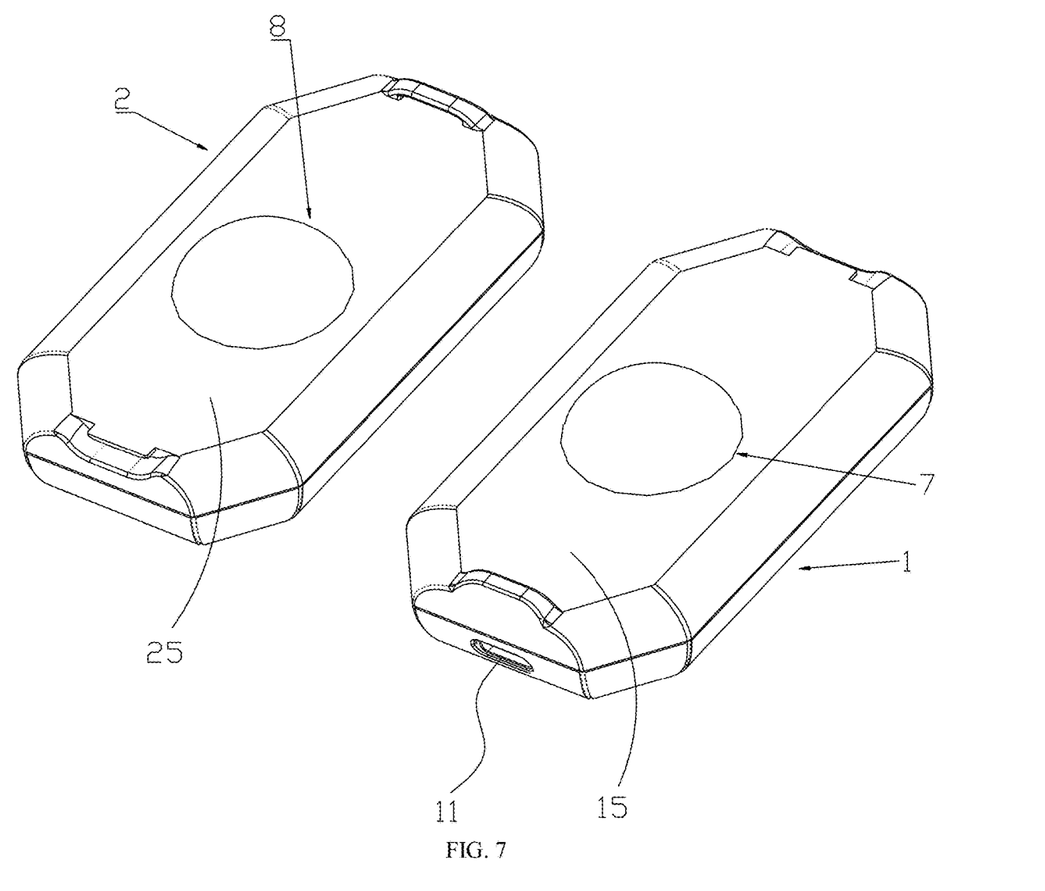
FIG. 7 is a schematic structural diagram of a magnetic attraction element and a magnetic attraction matching element.

Referring to FIG. 7, in some embodiments, the first connection part 3 is connected to the second connection part 4 by magnetic attraction. The first connection part 3 comprises a first magnetic attraction element 7. The second connection part 4 comprises a first magnetic attraction matching element 8. The first magnetic attraction element 7 and the first magnetic attraction matching element 8 are mutually attracted, so that the first connection inner surface 15 is attached to the second connection inner surface 25. The first hand warmer unit 2 and the second hand warmer unit 2 are combined into a whole.

The above description only describes embodiments of the present disclosure, and is not intended to limit the present disclosure, various modifications and changes can be made to the present disclosure. Any modifications, equivalent substitutions, improvements, etc. made within the spirit and scope of the present disclosure are intended to be included within the scope of the present disclosure.

What is claimed is:

1. A combined type hand warmer, comprising a first hand warmer unit and a second hand warmer unit, wherein the first hand warmer unit comprises a first outer surface and a first connection inner surface opposite to the first outer surface, the second hand warmer unit comprises a second outer surface and a second connection inner surface opposite to the second outer surface; the first connection inner surface comprises a first connection part, the second connection inner surface comprises a second connection part, and the first connection part is connected to the second connection part by buckling or magnetic attraction, so that the first connection inner surface is connected to the second connection inner surface, and the first hand warmer unit and the second hand warmer unit are combined into a whole, wherein the first connection part is connected to the second connection part by buckling, the first connection part comprises a first buckling part, the second connection part comprises a first buckle matching part, the first buckling part is detachably connected to the first buckle matching part, so that the first connection inner surface is buckled with the second connection inner surface, and the first hand warmer unit and the second hand warmer unit are combined into a whole;

wherein the first connection part further comprises a second buckling part, the second connection part further comprises a second buckle matching part, and when the first buckling part is detachably plugged into the first buckle matching part, the second buckling part is detachably plugged into the second buckle matching part;

wherein the first buckling part is a buckle or a buckle slot, the first buckle matching part is a buckle slot or a buckle, and when the first buckling part is a buckle, the first buckle matching part is a buckle slot; when the first buckling part is a buckle_slot, the first buckle matching part is a buckle; the second buckling part is a buckle or a buckle slot, the second buckle matching part is a buckle slot or a buckle, and when the second buckling part is a buckle, the second buckle matching part is a buckle slot; and when the second buckling part is a buckle slot, the second buckle matching part is a buckle.

2. The combined type hand warmer according to claim 1, wherein the first buckling part is a first buckle, the first buckle matching part is a first buckle slot, and the first buckle is detachably plugged into the first buckle slot.

3. The combined type hand warmer according to claim 2, wherein the second buckling part is a second buckle slot, the second buckle matching part is a first buckle, and when the first buckle is detachably plugged into the first buckle slot, the second buckle is detachably plugged into the second buckle slot.

4. The combined type hand warmer according to claim 3, wherein the first connection part further comprises a first positioning pillar, the second connection part further comprises a first positioning hole, when the first positioning pillar is located in the first positioning hole, the first buckle is detachably plugged into the first buckle slot, and the second buckle is detachably plugged into the second buckle slot.

5. The combined type hand warmer according to claim 4, wherein the first connection part further comprises a second positioning hole, the second connection part further comprises a second positioning pillar, and when the first positioning pillar is located in the first positioning hole and the second positioning pillar is located in the second positioning hole, the first buckle is detachably plugged into the first buckle slot, and the second buckle is detachably plugged into the second buckle slot.

6. The combined type hand warmer according to claim 5, wherein the first connection part further comprises a first guide slot, the first positioning pillar is located on an upper side of the first guide slot, the second positioning hole is located on a lower side of the first guide slot, the second connection part further comprises a second guide slot, the first positioning hole is located on an upper side of the second guide slot, the second positioning pillar is located on a lower side of the first guide slot, when the first positioning pillar slides into the first positioning hole along the second guide slot and the second positioning pillar slides into the second positioning hole along the first guide slot, the first buckle is detachably plugged into the first buckle slot, and the second buckle is detachably plugged into the second buckle slot.

7. The combined type hand warmer according to claim 3, wherein the first buckle is arranged on one side of the first hand warmer unit, the second buckle slot is symmetrically arranged on the other side of the first hand warmer unit; the second buckle is arranged on one side of the second hand warmer unit, and the first buckle slot is symmetrically arranged on the other side of the second hand warmer unit.

8. The combined type hand warmer according to claim 1, wherein the first outer surface of the first hand warmer unit is further provided with a first charging port, the first charging port is used for charging the first hand warmer unit; the second outer surface of the second hand warmer unit is further provided with a second charging port, and the second charging port is used for charging the second hand warmer unit.

9. A combined type hand warmer, comprising a first hand warmer unit and a second hand warmer unit, wherein the first hand warmer unit comprises a first outer surface and a first connection inner surface opposite to the first outer surface, the second hand warmer unit comprises a second outer surface and a second connection inner surface opposite to the second outer surface; the first connection inner surface comprises a first connection part, the second connection inner surface comprises a second connection part, and the first connection part is connected to the second connection part by buckling or magnetic attraction, so that the first connection inner surface is connected to the second connection inner surface, and the first hand warmer unit and the second hand warmer unit are combined into a whole, wherein the first connection part is connected to the second connection part by buckling, the first connection part comprises a first buckling part, the second connection part comprises a first buckle matching part, the first buckling part is detachably connected to the first buckle matching part, so that the first connection inner surface is buckled with the second connection inner surface, and the first hand warmer unit and the second hand warmer unit are combined into a whole;

wherein the first buckling part is a rotatable buckle, the first buckle matching part is a slot, and the rotatable buckle is detachably connected to the slot by rotating.

10. The combined type hand warmer according to claim 9, wherein a stop lug is arranged on the rotatable buckle, a stop edge is arranged on the slot, a notch is arranged on the stop edge, the notch is communicated with the slot, when the stop lug rotates to the notch with the rotatable buckle, the stop lug is placed in the screwing slot along with the rotatable buckle through the notch; when the stop lug is placed in the slot along with the rotatable buckle through the notch, the rotatable buckle is rotated so that the stop lug is rotated to stagger with the notch, the stop edge stops the stop lug of the rotatable buckle in the slot, and the first hand warmer unit and the second hand warmer unit are combined into a whole.

11. The combined type hand warmer according to claim 1, wherein a first power indicator is further arranged on the first hand warmer unit, the first power indicator is used for displaying the battery power of the first hand warmer unit; a second power indicator is further arranged on the second hand warmer unit, and the second power indicator is used for displaying the battery power of the second hand warmer unit.

12. The combined type hand warmer according to claim 1, wherein a first on/off button is further arranged on the first hand warmer unit, the first on/off button is used for controlling the first hand warmer unit to be turned on/off; a second on/off button is further arranged on the second hand warmer unit, and the second on/off button is used for controlling the second hand warmer unit to be turned on/off.

* * * * *